(12) United States Patent
Meltzer et al.

(10) Patent No.: US 9,955,869 B2
(45) Date of Patent: May 1, 2018

(54) SYSTEM AND METHOD FOR SUPPORTING HEALTH MANAGEMENT SERVICES

(71) Applicant: Purdue Pharma L.P., Stamford, CT (US)

(72) Inventors: Brian Meltzer, Wilton, CT (US); Sayee Natarajan, Wilton, CT (US)

(73) Assignee: PURDUE PHARMA L.P., Stamford, CT (US)

( * ) Notice: Subject to any disclaimer, the term of this patent is extended or adjusted under 35 U.S.C. 154(b) by 213 days.

(21) Appl. No.: 13/918,560

(22) Filed: Jun. 14, 2013

(65) Prior Publication Data

US 2014/0357961 A1 Dec. 4, 2014

Related U.S. Application Data

(60) Provisional application No. 61/831,138, filed on Jun. 4, 2013.

(51) Int. Cl.
| | |
|---|---|
| *A61B 5/00* | (2006.01) |
| *A61B 5/01* | (2006.01) |
| *A61B 5/11* | (2006.01) |
| *A61B 5/145* | (2006.01) |

(Continued)

(52) U.S. Cl.
CPC ......... *A61B 5/0002* (2013.01); *A61B 5/0022* (2013.01); *A61B 5/01* (2013.01); *A61B 5/112* (2013.01); *A61B 5/1112* (2013.01); *A61B 5/14532* (2013.01); *A61B 5/4842* (2013.01); *A61B 5/7275* (2013.01); *A61B 5/742* (2013.01); *A61B 5/747* (2013.01); *G06F 19/322* (2013.01);

(Continued)

(58) Field of Classification Search
CPC ......... A61B 5/01; A61B 5/0022; A61B 5/112; A61B 5/1112; A61B 5/14532; A61B 5/4842; A61B 5/7275; A61B 5/742; A61B 5/747; A61B 5/02055; A61B 5/1118; A61B 5/4833; G06F 19/322
USPC .................................................. 600/300–301
See application file for complete search history.

(56) References Cited

U.S. PATENT DOCUMENTS 4,803,625 A * 2/1989 Fu ....................... G06F 19/3418
128/906
5,897,493 A * 4/1999 Brown .......................... 600/300
(Continued)

*Primary Examiner* — John R Downey
*Assistant Examiner* — Shirley Jian
(74) *Attorney, Agent, or Firm* — Leason Ellis LLP

(57) ABSTRACT

A method in support of health management services acts upon active and passive data, in which the active data is communicated by a patient or healthcare professional and in which the passive data is detected by at least one sensor detectably coupled to the patient. These data are correlated with each other and if a predefined correlation is not met, further data can be solicited, patient-specific queries can be generated, alerts can be communicated, or a combination of these can be done in embodiments of the invention. Any Irregularity or trend in the data can be identified and processed in embodiments of the invention. Also in some embodiments, these data can be used in connection with intelligent, machine-based decisions to send communications concerning the provision of further healthcare resources to patients, such as in view of their relative acuity rank. Systems can be constructed to implement the methods described herein.

14 Claims, 6 Drawing Sheets

(51) Int. Cl.
  *G06F 19/00*     (2018.01)
  *A61B 5/0205*    (2006.01)
(52) U.S. Cl.
  CPC ......... *A61B 5/02055* (2013.01); *A61B 5/1118* (2013.01); *A61B 5/4833* (2013.01)

(56) References Cited

U.S. PATENT DOCUMENTS

| | | | |
|---|---|---|---|
| 5,933,136 A * | 8/1999 | Brown | G06F 19/3418 348/61 |
| 6,786,866 B2 * | 9/2004 | Odagiri | A61B 5/1118 128/920 |
| 6,893,396 B2 * | 5/2005 | Schulze et al. | 600/300 |
| 7,297,108 B2 * | 11/2007 | Iliff | G06F 19/322 128/920 |
| 7,594,889 B2 * | 9/2009 | St Ores | A61B 5/0031 600/301 |
| 7,789,828 B2 * | 9/2010 | Clapp | A61B 5/0002 128/920 |
| 8,398,546 B2 * | 3/2013 | Pacione et al. | 600/300 |
| 8,601,005 B2 * | 12/2013 | Bousamra | G06F 19/3475 600/365 |
| 8,616,895 B2 * | 12/2013 | Brown | 434/262 |
| 8,644,754 B2 * | 2/2014 | Brown | 434/350 |
| 8,655,259 B2 * | 2/2014 | Brown et al. | 434/350 |
| 8,734,339 B2 * | 5/2014 | Rao et al. | 600/300 |
| 8,758,238 B2 * | 6/2014 | Clapp | G06F 19/327 128/920 |
| 8,852,093 B2 * | 10/2014 | Clapp | G06F 19/327 600/300 |
| 2002/0019584 A1 * | 2/2002 | Schulze et al. | 600/300 |
| 2003/0083556 A1 * | 5/2003 | Cosentino | G06F 19/3418 600/300 |
| 2003/0187336 A1 * | 10/2003 | Odagiri | A61B 5/1118 600/300 |
| 2005/0113650 A1 * | 5/2005 | Pacione et al. | 600/300 |
| 2006/0030890 A1 * | 2/2006 | Cosentino | A61B 5/00 607/5 |
| 2006/0234202 A1 * | 10/2006 | Brown | 434/323 |
| 2007/0021979 A1 * | 1/2007 | Cosentino | A61B 5/0031 705/2 |
| 2007/0061167 A1 * | 3/2007 | Brown | 705/2 |
| 2007/0156457 A1 * | 7/2007 | Brown | 705/2 |
| 2008/0133269 A1 * | 6/2008 | Ching | G06F 19/328 705/2 |
| 2009/0164236 A1 * | 6/2009 | Gounares | G06Q 10/00 705/2 |
| 2009/0234916 A1 * | 9/2009 | Cosentino | A61B 5/0537 709/203 |
| 2009/0318773 A1 * | 12/2009 | Jung et al. | 600/300 |
| 2010/0082363 A1 * | 4/2010 | Warner et al. | 705/2 |
| 2010/0198608 A1 * | 8/2010 | Kaboff | G06Q 10/00 705/2 |
| 2010/0292545 A1 * | 11/2010 | Berka et al. | 600/301 |
| 2011/0105979 A1 * | 5/2011 | Schlaeper et al. | 604/5.01 |
| 2012/0191147 A1 * | 7/2012 | Rao et al. | 607/3 |
| 2014/0073883 A1 * | 3/2014 | Rao et al. | 600/301 |
| 2014/0236249 A1 * | 8/2014 | Rao et al. | 607/6 |
| 2014/0357961 A1 * | 12/2014 | Meltzer et al. | 600/301 |

* cited by examiner

SYSTEM AND METHOD FOR SUPPORTING HEALTH MANAGEMENT SERVICES

This patent application claims the benefit of priority from U.S. Provisional Patent Application Ser. No. 61/831,138, filed on Jun. 4, 2013, entitled "A SYSTEM AND METHOD FOR SUPPORTING HEALTH MANAGEMENT SERVICES," which is hereby incorporated by reference as if set forth in its entirety herein.

TECHNICAL FIELD OF THE INVENTION

This patent application relates generally to the field of health management and, in particular, systems and methods that provide support for improved monitoring, diagnosing and treatment of chronic illnesses.

BACKGROUND OF THE INVENTION

Technical advances and increasing ubiquity of mobile phones have paved the way for new advances in the treatment and management of chronic illnesses. Researchers and clinicians have identified several areas in which mobile phones could transform care for the chronic illness patient, including improved adherence, better data about what patients do and how they feel between visits, and feedback and tools to assist the patient in the management of their illness. However, presently available systems to date utilizing mobile phones are either non-scalable academic endeavors or unproven commercial applications, and do not adequately support the endeavors of healthcare providers.

In the current world of chronic illness management, patients typically are seen on a monthly to every-three-month clinical visit schedule. At the time of the visit, patients are typically surveyed about their symptoms and overall functional status over the time interval between visits. This is prone to errors of oversimplification and poor subjective recall. For example, patient recall of pain, affect, and satisfaction is notoriously poor. A patient may report that their pain over the last month was significant and that they were generally not very happy, but collected data may paint a very different picture.

Presently there are no suitable options for providing the patient and clinician/healthcare professional a more accurate view of how a patient is functioning in the presence of chronic illness. For example, chronic pain is ideally managed in a multi-modal fashion. In addition to prescribing analgesics, clinicians typically prescribe non-pharmacologic interventions like diet, exercise, physical therapy, etc. There is, however, no currently available means for providing support for all-encompassing health management services to help patients and clinicians manage all these related treatments.

It is with respect to these and other considerations that the disclosure made herein is presented.

SUMMARY OF THE INVENTION

Technologies are presented herein in support of a system and method for supporting health management services.

According to a broad aspect of the invention, a method in support of health management services receives both active and passive data. The passive data is detected by at least one sensor that is detectably coupled to a patient and can comprise, for example, fitness, position, or biological state data. The received data is correlated with each other and if a predefined correlation is not met, further patient-specific queries or alerts are generated and communicated over a network connection to a device of the patient. The data can also be processed to identify any irregularity in the data and generate patient-specific queries in the event that a predefined irregularity is identified.

According to a more particular aspect of the invention, a method in support of health management services for a patient includes the step of receiving, at a server having a processor and memory, passive data detected by at least one patient sensor that is detectably coupled to the patient. The server has a processor which has code that generates a first patient-specific query for delivery to the patient. Active data provided by the patient is received at the server in response to the first patient-specific query. The received active data is correlated by code executing in the processor with the received passive data. In response to a failure of the correlation to meet a predefined correlation threshold, the server solicits at least one of further active data and further passive data using code executing in the processor.

Methods in accordance with more particular aspects of the invention can include further steps. For instance, the server can receive further active data and/or passive data in response to the soliciting, and can repeat the step of correlating the received active data with the received passive data. Likewise, methods in accordance with more particular aspects of the invention can generate a notification reflecting a failure when the server fails to correlate the active data and passive data to meet the predefined correlation threshold, and provide the notification to at least one of the patient, a healthcare professional, and a third-party. Alternatively or in addition, notifications can be generated that reflect a successful correlation of the received active data with the received passive data; and can likewise be provided to at least one of the patient, a healthcare professional, and a third-party.

In yet a further aspect of the invention, methods can include steps that process received data to anonymize it and provide outputs that are based on anonymized data. In still yet a further aspect of the invention, methods can be arranged to influence whether and when to schedule patient appointments with healthcare professionals so as to provide care when a critical-level indicator is generated in association with a patient. Also, critical-level indicators can influence priority of one patient over another in connection with scheduling appointments with healthcare professionals.

Methods in accordance with still further aspects of the invention can include steps that identify any predefined irregularities in the received active data and the received passive data. In response to the identification of at least one predefined irregularity in the received active data or in the received passive data, the server generates a second patient-specific query for delivery to the patient using code executing in the processor. As with the correlation step, in still further aspects of the inventions, the server can generate a notification reflecting an irregularity when one is detected and/or generate a notification when no irregularities are detected, and provide the notification to at least one of the patient, a healthcare professional, and a third-party.

In a variation of one or more of the foregoing aspects, a method in support of health management services includes the step of receiving at a server passive data detected by at least one sensor that is detectably coupled to a patient. The server has a processor which has code that generates a first patient-specific query. Active data provided by the patient is received at the server in response to the first patient-specific query. The received active data is correlated by code executing in the processor with the received passive data. In response to a failure of the correlation to meet a predefined correlation threshold, the server generates an alert, and communicates at least one of the first patient-specific query and the alert over a network connection to a device of the patient.

According to yet another broad aspect of the invention, a system includes a server having a processor and memory, a network connection configured to communicate over a network to a device of the patient, and a plurality of code sets that are executable in the processor and which, when executed, configure the processor to implement the functional steps in the methods described above.

In a more particular aspect, a system in support of health management services for a patient of the type who has at least one passive sensor detectably coupled to the patient to gather data therefrom is provided. The system comprises a server having a processor and memory, a network connection configured to communicate over a network to a device of the patient, and a plurality of code sets that are executable in the processor and which, when executed, configure the processor to: receive passive data detected by at least one sensor; generate a first patient-specific query; receive active data provided by the patient in response to the first patient-specific query; correlate the received active data with the received passive data; and, in response to a failure of the correlation to meet a predefined correlation threshold, solicit at least one of further active data and further passive data.

In a further aspect of the invention, the system can be configured to identify any predefined irregularities in the received active data and the received passive data; and generate a second patient-specific query in response to the identification of at least one predefined irregularity in the received active data or in the received passive data. In accordance with further aspects, the network connection to the device comprises a connection which is in communication with the at least one passive sensor.

In accordance with still another aspect of the invention, a method in support of analyzing health management services of the type provided by a plurality of healthcare professionals who are each affiliated with one or more healthcare networks is described. The method operates under control of a processor that is configured by code executing therein to correlate separate sets of data received from each of a plurality of patients of the type described above, namely, the active data which is provided responsive to data queries and passive data provided by an electronic device associated with respective patients. The correlations are mapped to one or more symptoms and stored in a database in association with each patient and in association with at least one healthcare professional. A set of patients among the plurality of patients is identified who have a trend of changes in the correlations for a particular symptom or any failure of the correlation to meet a predefined correlation threshold for the particular symptom. The set of patients are ranked in order of most acute to least acute, and a communication over a distributed computer network is made to either the healthcare professional or the healthcare network affiliated with the healthcare professional that further resources are to be provided to at least a portion of the ranked patients based on the ranking.

In an optional, further aspect of the foregoing method, at least one intervention by the healthcare professional with the patient can be scheduled after the communicating step.

These and other aspects, features and advantages will be understood with reference to the following description of certain embodiments of the invention.

DETAILED DESCRIPTION OF CERTAIN EMBODIMENTS OF THE INVENTION

Figure 1:
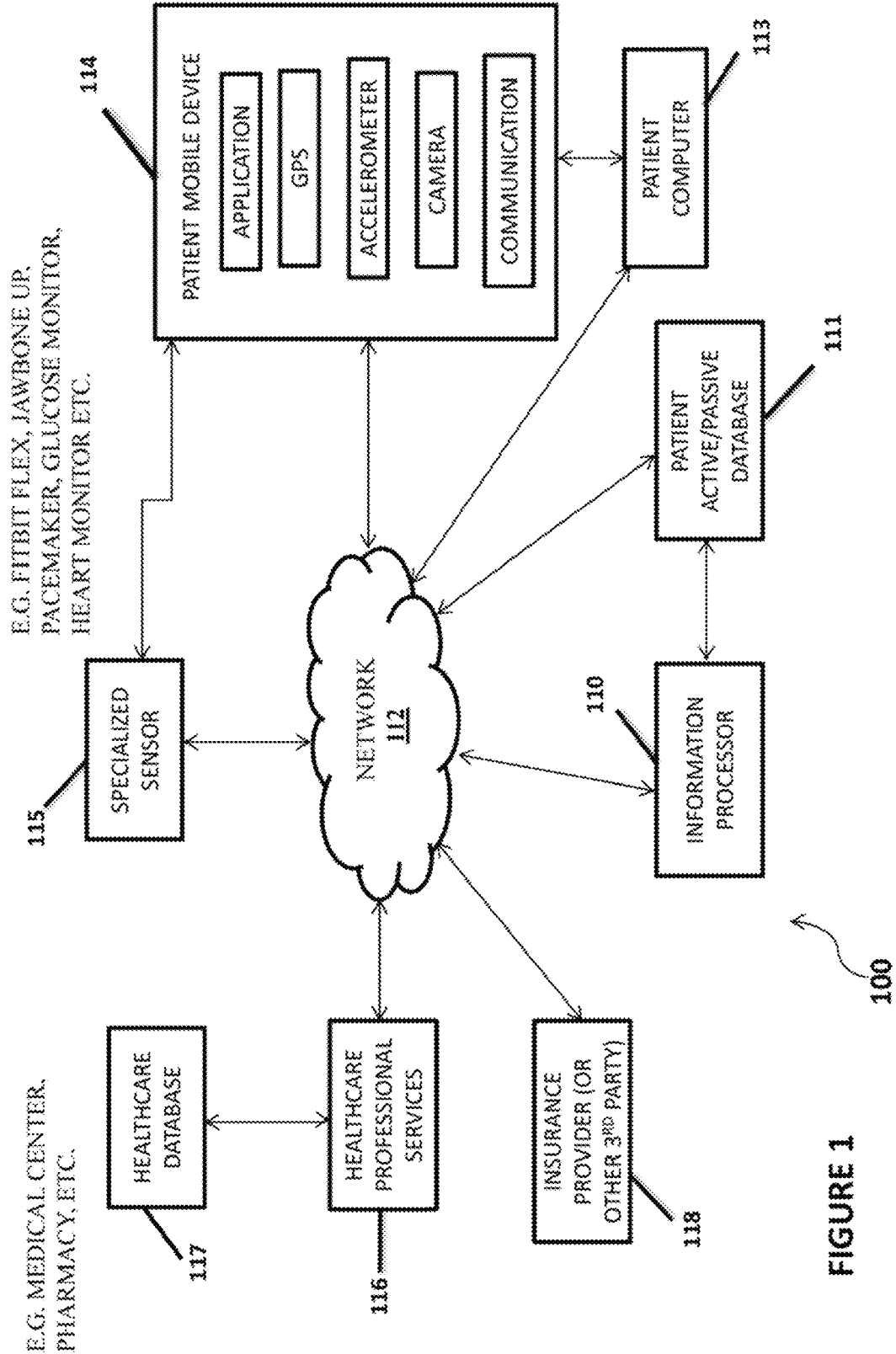
FIG. 1 is a high-level diagram illustrating an exemplary configuration of a system for supporting health management services according to at least one embodiment of the invention.

By way of overview and introduction, various systems and methods are described herein that facilitate the support of healthcare management services by using sensors that are widely available in smartphones, wrist bands and other commercial devices to gather data in a passive manner and correlate the collected passive data with clinically validated survey instrument data gathered in an active manner via an application on the patient's mobile device and/or over the Internet from a computer. By correlating information that is provided by the person passively with information concerning the same general moment in time that is provided actively, that is, in response to a survey/question/affirmative input by the person, a richer data set results which is useful to many third parties including physicians, pharmacists, and payors in providing and assessing healthcare to that person, or to anonymized persons that share demographics. This can provide the patient and clinician a more accurate view of how a patient is functioning in the presence of a chronic illness, such as chronic pain.

Systems and methods described herein are designed to (1) collect higher resolution, more meaningful data regarding a patient's health and health-related behavior, including adherence, (2) provide patients with feedback and guidance for managing their pain, and (3) provide clinicians with synthesized, understandable reports based on data collected. An overarching goal is to transform the way chronic illness is managed in the ambulatory care as well as other healthcare settings.

Additionally, by tracking a patient longitudinally over time using sensors, the various systems and methods provided herein can monitor when a patient is moving physically, as well as "check in" a patient at a particular location, such as at a physical therapy office. By monitoring other data associated with the patient, such as with an individual patient's shopping loyalty cards, the various systems and methods provided herein can track the patient's grocery shopping and determine the "types of calories" that the patient is consuming, and provide critical data back to the patient, and/or to a healthcare professional or third party payor (e.g. an insurance company).

Types of data that may be collected actively include, but are not limited to: pain surveys, functionality surveys, medications prescribed/taken, adherence, allergies, side effects and adverse events, questions involving diet and nutrition, sleep quality, questions involving exercise, questions that are driven by analysis of data collected on a patient, but which are designed to change a patient's behaviors towards active self-management, etc. It should be noted that while active data will typically be provided by the patient, in some embodiments such active data may be provided by others associate with the patient, such as a family member, caregiver, or a healthcare professional. Active data may be collected, for example, in the form of affirmative/negative responses (e.g., "yes" or "no" responses to questions), which can be converted to "1's" and "0's" and stored in a database in numerical form. Additionally or alternatively, data may be stored in alpha-numeric string form (e.g., "I have been running a high fever today"), which can be processed by a natural language processing algorithm with the terms and phrases in the collected data being weighted, as described more fully below, and which can yield different analysis results than more direct affirmative/negative correlative data. Finally, active data may also be provided directly in numeric form (or an alphabetic/symbolic equivalent), either as a value on a scale, or as a representation of a calculation. For example, a query sent to a patient might ask, "On a scale of one-to-ten (1-10), what do you believe to be an accurate representation of your level of pain today?" Alternatively, a query might ask, "How many times have you eaten today?" In either case, the expected response will be a numeric value inputted by the patient.

Types of data that may be collected passively include, but are not limited to: location, movement and acceleration, ambient temperature, pedometer data, heart rate, blood pressure (i.e., biological state data) electronic medical records, laboratory records, third-party claims data, pharmacy and PBM records, grocery receipt contents, and other sensors, such as wireless scales, wireless blood glucose meters, wireless pacemakers, and other medical sensor devices, etc. Other techniques for passively analyzing data, such as employing Natural Language Processing (NLP) on patients' communications, and analyzing data entry patterns, may also be used. More generally, a variety of passive sensors, as that term is used in the present specification, can be employed to capture data while a person is engaged in a variety of activities, including working, playing, eating, resting and sleeping. Together with the capture of any of the foregoing forms of passive data is metadata concerning the time that the data was captured, and this metadata is provided to a data service and stored so that the passive data can be correlated with active data of the same person (concerning the same general point in time) in support of the identification of any variance outside of a predefined correlation threshold, or in support of an identification of a change from a baseline value or range for the patient or one associated with a demographic that includes the patient. Examples of passive data collected by sensors in this manner may include, for example, Global Positioning System (GPS) coordinates, a body-temperature measurement, a blood-sugar level readout, a number of steps taken, etc., along with a metadata time-stamp of when the data was collected.

Furthermore, by collecting large amounts of data from various sources and analyzing them through databases designed to function by analyzing unstructured data (so called "Big Data"), insights are gained into the behaviors and functionality of the chronic illness patient that are not currently obvious to the examining physician, the patient or anyone closely related to the patient. This is critical, as some data are simply very difficult for clinicians to obtain, such as when a patient becomes non-adherent with a given therapy and why. Other examples include noting when pain levels and function change significantly and what external factors may be responsible for those changes.

The output of these analyses can serve to provide active feedback to the patient with the goal of encouraging the patient to actively monitor the patient's own care. As an example, if a chronic pain patient is prescribed physical therapy as part of their treatment plan, the various systems and methods described herein would monitor compliance. A physician would be able to tell if the patient has checked in to their physical therapist's office, and would be able to track, via sensors residing with the patient, if the patient is moving during their physical therapy session. The physician would also be able to corroborate a visit to the physical therapist's office with claims data generated by the visit. All the while, the patient is provided with questions about their pain and their functionality. The system then pulls all of this data together and makes an assessment as to whether physical therapy is helping the patient. To further the example, if a patient's pain is managed well, and the system may determine that the patient is compliant with all pharmacologic and non-pharmacologic parts of his treatment plan, and it may become relatively obvious when a patient is no longer feeling well. If the patient is no longer doing well, modules that are configured by code executing in one or more processors can cause the system to detect if the patient has been compliant and, if not, remind the patient to adhere to the parts of the treatment plan that are currently not being complied with.

Embodiments of the system described herein can be implemented to provide at least three different types of health management functions for a particular patient, a plurality of patients under the care of a healthcare provider, and/or a plurality of healthcare providers in an Accountable Care Organization/Integrated Deliver Network: (1) active-treatment-plan-related functions, (2) compliance-related functions, and (3) patient-veracity-related functions. Active-treatment-plan-related functions can include, for example, providing reminders to a patient to take medication in a timely manner, and helping the patient follow a treatment plan. Compliance-related functions can include, for example, verifying individual events and/or statements associated with a patient. Patient-veracity-related functions can include, for example, evaluating longitudinal data to assess a general level of adherence to truth and conformity to facts.

It should be noted that while many examples provided herein refer to chronic pain management, the systems and methods provided herein can be equally applicable to management of other chronic diseases. The ability to use "big data" approaches to tracking patients, providing self-management insights, and communicate back to a clinical care team should be of value to many important chronic diseases including, but not limited to: congestive heart failure, diabetes, asthma and COPD, rheumatoid arthritis, cancer, and HIV/AIDS, etc.

Furthermore, in addressing the challenges associated with managing chronic illnesses, the systems and methods described herein use computational and statistical techniques to synthesize meaningful and actionable information from the raw data. For example, rather than providing raw accelerometry or even daily activity level reports, a better metric may be the number of days in the last two weeks in which a patient was active for a specified period of time (e.g., 3 hours).

Additionally, using the disclosed systems and methods, healthcare professionals can determine what data patients with chronic illnesses are interested in gathering related to their health and care. Data that the patients are interested in seeing and exploring for themselves, such as what do they do on a day-to-day basis that corresponds with better function and less pain, are provided via a feedback module. Code executing in an information processor causes the system to synthesize collected data by identifying irregularities in the active and passive data collected and by correlating the active data with the passive data. The system can then, for example, present selected elements of the synthesized data in the form of feedback to a health monitoring application or other messaging system accessible by, or operating on, a mobile device or computer of the patient. A user interface helps the patient visualize progress with treatment, reflect on how they feel, and gain insight and connections between care, activities, and the management of their pain.

The user interface may also provide features allowing the patient to respond to the data with any questions or comments for the patient's healthcare professional, either directly referencing the presented data, or by providing a general health related query. Feedback may also be coupled with other resources when presented to a patient, which may help encourage the patient to more actively manage his or her health independently. For example, data reflecting an irregularity in a patient's heart-rate may be coupled with a link to information and other resources related to high blood pressure, heart-attach recognition, etc., while also providing a link to a service that can contact Emergency Medical Services (EMS) if necessary. Additionally, other patient self-management tools, educations modules, social interaction tools, recommendations, and accountability measures can also be provided to the patient along with the feedback. Finally, in some embodiments, the feedback may also be in the form of a command (e.g., code to be executed in a processor of the patient's mobile device) that automatically causes the patient's mobile device to perform a specific function. For example, if a patient is unresponsive to a request for active data (e.g. a patient does not respond to a Healthcare Professional-generated query), and correlated passive data from an accelerometer indicates that the patient has not moved for a predefined period of time, the command in the feedback may cause the patient's mobile device to activate a GPS embedded in the device or another patient sensor, so that the patient's location can be known in the event the patient is determined to be in danger.

The systems and methods described herein also have application in patient population management from the perspective of an Accountable Care Organization (ACO), Integrated Delivery Network (IDN), Hospital Network, clinical care team and/or any other healthcare professional or group of healthcare professionals. As care for patient populations transitions from fee-for-service to accountable care, clinical care teams and healthcare professionals require tools to help manage their patient populations in a manner that more effectively allows for resource utilization planning. The systems provided herein are intended to be a platform that is provided to a patient as part of the pain management treatment plan. That is, in addition to a prescription and a referral to physical therapy, etc., a patient may also be prescribed the healthcare management system itself. Furthermore, the systems provided herein are also intended to help ACOS, IDNs, and other hospital/healthcare networks determine which practices/segments of their networks are providing the best care delivery, and/or are having the most success in helping patients manage their health. This "real world" analysis of best practices will allow for the ability of the various networks to determine and deliver feedback and/or guidelines for best care practices to the rest of their healthcare professional communities within each network and/or across networks.

For all of the patients in a practice that are followed on this healthcare management system, in accordance with a further aspect of certain embodiments of the system, a portal is enabled through an API which provides a "dashboard" to the clinical care team that will alert them to the patients who are in need of being seen sooner, rather than later. Patients who are doing well will be indicated as such on the dashboard. They likely do not need to be seen, other than for a regular check-up. This will allow for much more appropriate, "just-in-time" resource allocation to patients who need care. This allows clinical teams to care for patients that, in fact, threaten the practice's quality and performance scores. In turn, this proves valuable in managing a practice, Integrated Delivery Network or Accountable Care Organization's profit and loss statement.

As an example, chronic pain is a therapeutic area of practice that has significant unmet needs in terms of standard treatment protocols and methods of managing patients. Using "big data" approaches to analyze multiple streams of patient data, population-based patterns can be discerned that can lead to treatment algorithms for individual patients based upon similarities in the characteristics of multiple patients.

Turning now to FIG. 1, the schematic block diagram illustrates a distributed network 100 including an information processor 110 constructed in accordance with one or more implementations of the invention. The information processor communicates over a network 112 with multiple other processing machines such as computers, and more specifically stationary devices, mobile devices, and computer servers. Communication can be either direct or indirect through further machines that are accessible to the network 112. The network 112 can comprise the Internet, one or more telephony networks, one or more network segments including local area networks (LAN) and wide area networks (WAN), or a combination thereof.

Among the devices on the network are user devices which can include stationary device 113 such as desktop computers, kiosks and other machines, each of which generally is understood in the art as having one or more processors configured to execute code to implement a variety of functions, a computer-readable memory, one or more input devices, one or more output devices, and a communication port for connecting to the network 112. One of many functions that can be implemented on such devices is the execution of a browser software application. Browsers enable retrieval, presentation and navigation of information resources on the World Wide Web or on web servers in private networks, and of files in file systems. In FIG. 1, one stationary device—patient device 113—is illustrated, though the stationary device does not necessarily have to belong to the patient; rather, this simply indicates the patient's ability to access and use the stationary device, either directly or indirectly via another person. Furthermore, patient device 113 may be a computer, kiosk, or any other electronically communicative stationary device. Among other devices on the network is patient mobile electronic device 114 ("mobile device" or "MED"), which is generally understood in the art as having hardware components as in the stationary device 113, but which may further include componentry such as near field communications (NFC) circuitry, gyroscopes, inertia detection circuits, geolocation circuitry, among other sensors. Examples of typical MEDs are smartphones, personal digital assistants, tablet computers, and the like, which can communicate over cellular and/or Wi-Fi networks or using a Bluetooth or other communication protocol.

Additionally or alternatively, mobile devices may include more specialized sensors, which may function in parallel with typical mobile devices or as "stand-alone" sensing equipment, represented as specialized sensor 115 in FIG. 1 for use in passive data capture. Common examples include wireless pedometers/trackers (e.g. Fitbit Flex, Jawbone Up), GPS units, and wireless medical monitoring equipment, such as pacemakers, heart monitors, and glucose monitors, which may communicate directly over network 112 or via a connection to mobile device 114. As well, the input devices associated with conventional smartphones such as microphones, accelerometers, touch screens, light meters, digital cameras, and the input jacks that enable attachment of further devices such as thermometers and so on can comprise a "specialized sensor." In short, it should be appreciated that a patient sensor can comprise a variety of conventional sensors and that the "specialized" nature of the sensor can be simply the specialized application to the embodiments disclosed herein as opposed to a sensor of unique construction—which is not required in many embodiments of the present invention, though special-purpose sensors can be employed in particular implementations of the invention. In FIG. 1, one mobile device 114 and one specialized sensor 115 are illustrated, both associated with a single patient. In practical implementations of the invention, there can be a multiplicity of stationary and mobile devices 113, 114, and 115 more generally referred to herein as user devices. The illustrated embodiment depicts use of conventional sensors in a specialized application in connection with the following discussion. It should be noted that while specialized sensor 115 and mobile device 114 are described herein as both being associated with the same patient, in other embodiments different devices and/or sensors may be directly associated with different patients. Also, passive data from the different devices and sensors (and the data they generate) can still be correlated with each patient by indirect association. For example, implementations of this system can provide for a husband and wife to have their devices, sensors, and collected data linked, so that a physician monitoring the couple can has access to a greater pool of data.

Among the computer servers that are accessible to the network 112 and which communicate over the network to the user devices are machines that are configured to provide content to the user devices and retrieve data from the user devices. The content can include information in a variety of forms, including, as non-limiting examples, text, audio, images, and video, and can include embedded information such as links to other resources on the network, metadata, and/or machine executable instructions. Each computer server can be of conventional construction, and while discussion is made in regard to servers that provide different content and services to users, one or more of the servers can comprise the same machine or can be spread across several machines in large scale implementations, as understood by persons having ordinary skill in the art. In relevant part, each computer server has one or more processors, a computer-readable memory that stores code that configures the processor to perform at least one function, and a communication port for connecting to the network 112.

The content can be provided by a healthcare professional services (HP) server 116, and may include information relevant to management of the patient's health, HP-generated surveys, emergency notification information, appointment information, etc. In some embodiments, a HP-generated survey may be a standard question or group of questions relating to a particular chronic illness, treatment, symptom, or patient demographic, such as the type of form survey distributed to patients during a visit with a physician. Alternatively, as explained in more detail below, an HP-generated survey may be more personalized for the particular patient. HP server 116 can also retrieve and push data to and from other devices and servers connected to network 112, and from data repositories, such as healthcare database 117. Healthcare database 117 may be a medical records database of a medical center, hospital, or pharmacy, for example, and may be connected directly to HP server 116 (as shown) or indirectly via network 112. A third party server, such as Insurance Provider server 118, may also send and retrieve content or other data via network 112. It should be noted that while in this exemplary embodiment the third party server is an insurance provider server, any other relevant third-party server may also be included, such as other third party payors, educational institutions, government agencies, etc.

Patient computer 113, mobile device 114, specialized sensor 115, HP server 116, and insurance provider server 118, are all configured to communicate with information processor 110 as necessary, either directly or indirectly. Information processor 110 further includes memory for data storage, such as patient active/passive database 115, which will be explained in further detail below. The information processor 110 operates on the content of such communications with patient computer 113, mobile device 114, specialized sensor 115, HP server 116, and insurance provider server 118, as the case may be, to implement the various implementations described herein.

Figure 3:
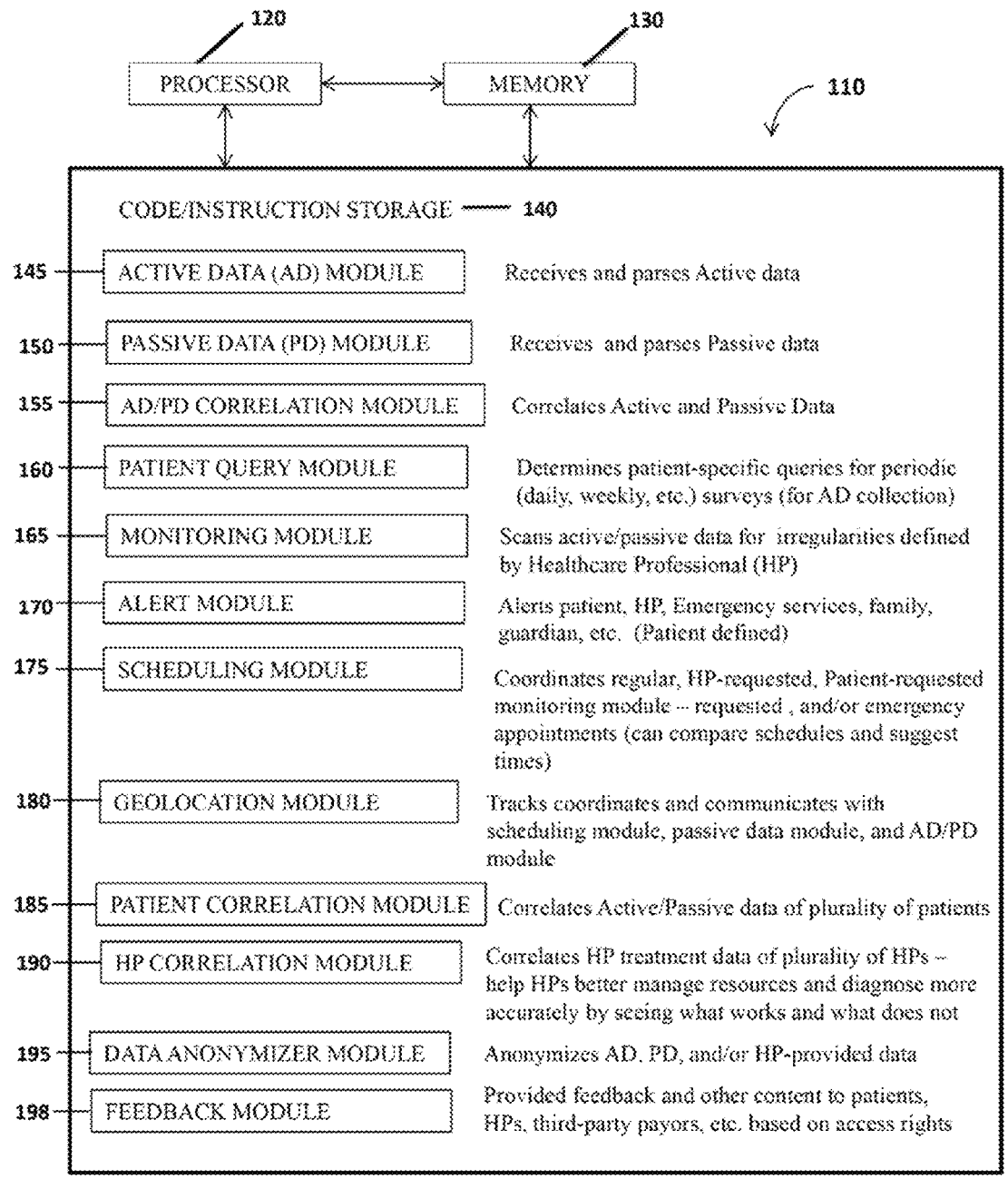
FIG. 3 is a block diagram illustrating an exemplary configuration of a system for supporting health management services according to at least one embodiment of the invention.

With brief reference to FIG. 3, the information processor 110 can comprise a server of the type described above, and has a microprocessor 120 ("processor") that communicates with at least a first memory portion 130. Multiple storage devices are also contemplated, and can reside in the same location or in multiple locations. In relevant part, the information processor includes in its memory computer code that executes in the processor 120 and thereby configures the processor 120 to operate on communications and digital data as described more fully herein below. The code can comprise one or more programs, libraries, functions or routines which, for purposes of this specification, are described in terms of a plurality of modules, residing in a representative code/instructions storage 140, that implement different parts of the process described herein. In particular, the following modules are discussed, in terms of their functionality and the manner of defining each module, in the paragraphs that follow: an active data (AD) module 145, a passive data (PD) module 150, an AD/PD correlation module 155, a patient query module 160, a monitoring module 165, an alert module 170, a scheduling module 175, a geolocation module 180, a patient correlation module 185, an HP correlation module 190, a data anonymizer module 195, and feedback module 198. It will be appreciated, however, that a given implementation can be achieved with fewer modules combining several functionalities described herein in relation to individual modules, or with more modules and additional functionalities.

Figure 2:
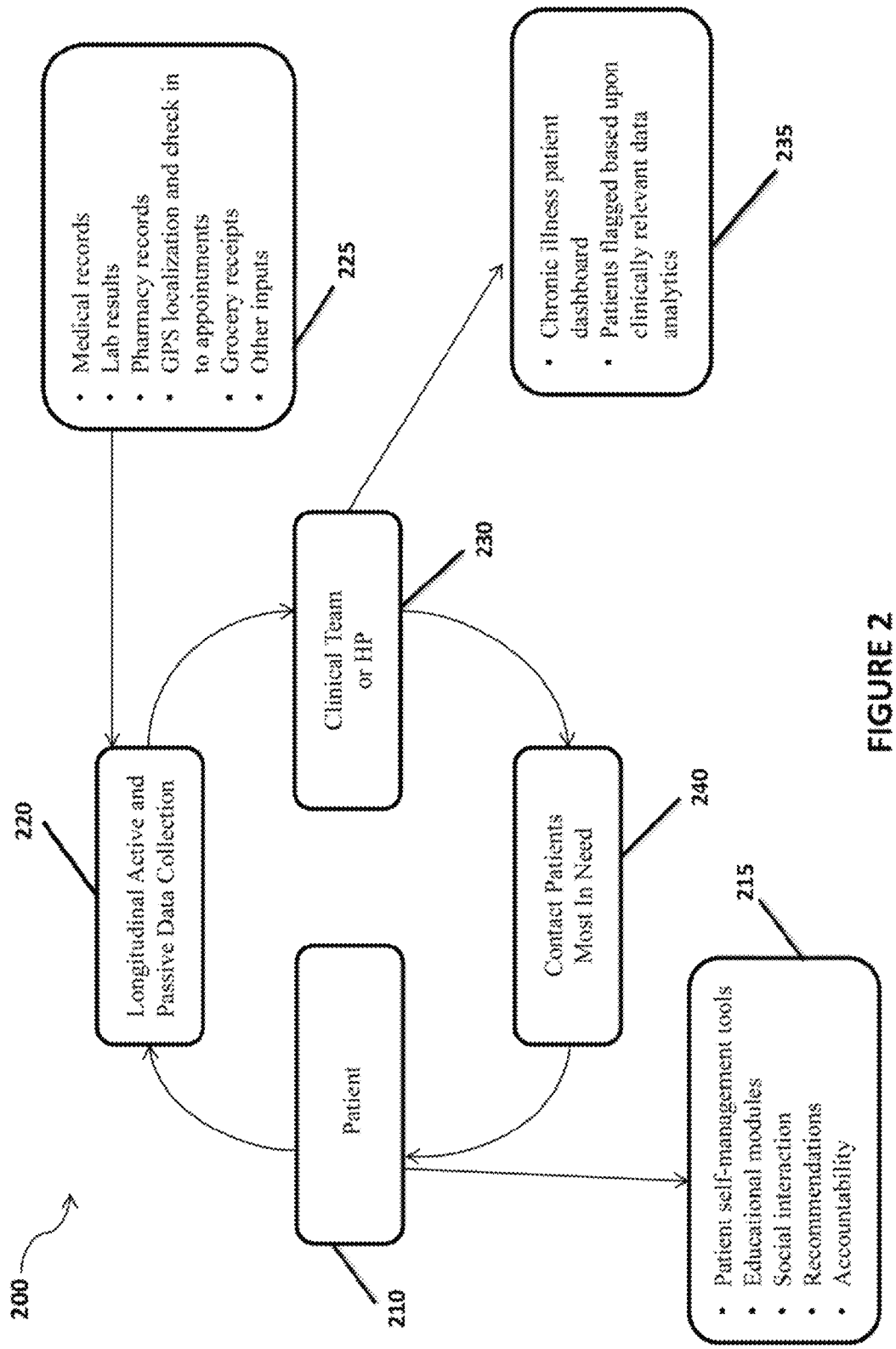
FIG. 2 is a high-level flow diagram illustrating elements of a method for supporting health management services according to at least one embodiment of the invention.

Turning now to FIG. 2, a high-level flow diagram illustrating elements of a "closed loop" method 200 for supporting health management services according to at least one embodiment of the invention is provided. Through the support of distributed network 100, patient 210 provides longitudinal active and passive data 220 to an HP or clinical team 230. The clinical team 230 can then determine which patients are most in need of attention and contact a patient, such as patient 210, as required, 240. Patient 210 is provided with feedback and other resources 215, such as patient self-management tools, educations modules, social interaction tools, recommendations, and accountability measures. Patient 210 generates longitudinal active and passive data 220 via a variety of sources 225, such as medical records, lab results, pharmacy records, GPS localization and check-in to appointments, grocery receipts, digital sensors, and other inputs. Finally, clinical team 230 can manage multiple patients' healthcare with resources 235, such as a chronic illness patient dashboard, and monitors for flagging patients based upon clinically relevant data analytics, etc.

In this closed loop, a plurality of patients generate data, HPs analyze and monitor the data of each patient, feedback is generated for each patient, and the feedback is provided back to the patient along with other helpful information. This encourages better self-management for the patient, while allowing the HP to maximize resources in the healthcare management of numerous patients. However, as will be explained in detail below, in accordance with a salient aspect of the invention, this closed loop can be opened to provide additional benefits for both the patient and the HP.

Figure 4:
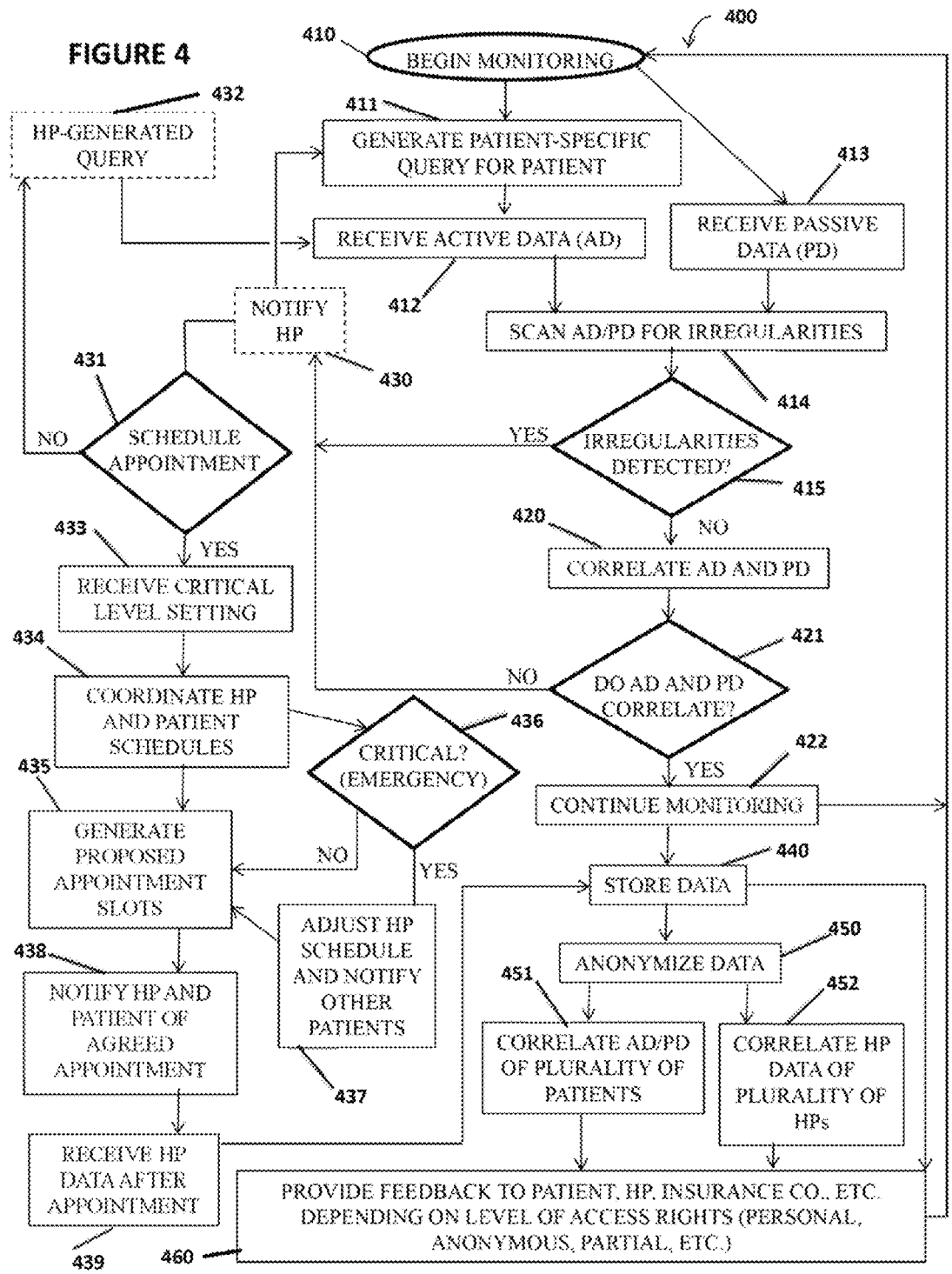
FIG. 4 is a flow diagram illustrating a process for supporting health management services according to at least one embodiment of the invention.

Turning now to FIG. 4, a flow diagram illustrating a routine 400 for supporting health management services according to at least one embodiment of the invention is provided. At step 410, processor 120 executes computer memory code represented by monitoring module 165, to begin monitoring patient 210. In doing so, patient query module 160 generates one or more patient-specific queries to provide to patient 210. Patient-specific queries are used primarily in the collection of active data in the form of periodic surveys. In some embodiments, a survey may be a single generic or patient-specific query or a set of generic and/or patient-specific queries which are delivered to the patient's mobile device 114 and/or patient computer 113 over network 112 and displayed for the patient. Queries can be propagated as a list, group, or as individual queries, and can be delivered simultaneously or one after the other as defined by the patient and/or HP. In some embodiments, each survey can have one or more related or unrelated queries.

These surveys can be delivered to the patient on a schedule, e.g., hourly, daily, weekly, monthly, etc., as the patient and/or HP 230 sees fit. In some embodiments they can be in the form of a text message, e-mail or any other digital communication as is appropriate. Alternatively or additionally, queries can be delivered via an application or widget operating on mobile device 114 and/or patient computer 113. For example, in some embodiments an application resident on mobile device 114 may be configured to receive patient-specific queries and provide them to the patient on a display with a user interface (UI). The patient 210 can then respond via the UI and associated application. In some embodiments, patient 210 may be provided a patient-specific query via one mode of communication, and respond via a second mode. For example, patient 210 may receive an e-mail containing the patient-specific query, and the email may contain a link to a webpage where patient 210 can reply to the patient-specific query.

In some embodiments, patient 210 may be prompted to provide a vocalized (speech) response to a patient-specific query, so that data can be extracted from the patient's speech. The response is converted to text so that its substance can be processed like any other textual response. In some implementations, a natural language processing (NLP) algorithm is used to establish an expected response signal which can include interim operations before the expected response signal is established. The interim operations performed by the natural language processing algorithm can be based on statistical machine learning in which a learning algorithm based on, say, statistical inference, is used to automatically learn rules through the analysis of large textual corpora of examples, preferably an annotated corpora that includes part-of-speech tagging (in which information about each word's part of speech (verb, noun, adjective, etc.) is added to the corpus in the form of tags) or the lemma (base) of each word. The automatically learned rules can then be applied to the inputted features included in the text of the responses of by patients and digital data provided to the information processor 110. Such rules, as understood in the art of NLP, apply statistical models which make probabilistic decisions based on real-valued weights that are associated with each input feature. Statistical models of this type can express the relative certainty of different possible answers rather than only one, and thereby produce more reliable results. As such, the interim operations in such implementations provide weightings to a set of probabilistic decisions so that those decisions that have the highest weightings are selected for the determination of as to an aspect of the relative health of the patient, with the expected response signal being established based on those decisions. A single decision with the highest rating can be selected, or the results with the highest statistical likelihood of pertinence can then be compared to a hard-coded rule base for a match within prescribed criterion (criteria) in order to establish the expected response signal.

In some embodiments, patient-specific queries may be generalized queries that are selected and/or modified and provided based on patient-specific data, or may be generated directly from patient-specific data. Patient-specific queries may include pain surveys, functionality surveys, medications prescribed/taken, adherence, allergies, side effects and adverse events, questions involving diet and nutrition, sleep quality, questions involving exercise, etc. Furthermore, patient-specific data used in selecting patient-specific queries may include information regard the health, age, sex, disposition, demographic, treatments provided, or any other characteristic associated with the patient. It should be noted that patient 210 may also choose to provide AD without prompting from a query.

As explained above, in some embodiments, a survey can comprise one or more generic and/or patient-specific queries, and a query can take different forms which may elicit different types of responses. A query may ask a patient to respond to the query by entering a response via the UI. Depending the query, the response requested may be in the form of a single number value, an alpha-numeric string of text, available input such as speech and/or a gesture, such as "dragging" or pressing an image, icon, link, or text etc. displayed on the UI. In some embodiments, a query may request the performance of an action that would be recorded by one or more sensors and stored as passive data. For example, a query may ask a patient if the patient is able to take five (5) steps and to report an assessed level of pain associated with performing the action of taking the steps. In such an example, AD related to the level of pain ascribed by the patient, and PD related to the actual movement of the patient, are collected in real time in response to the query, at which point the data collected can be correlated.

Patient-specific queries may initially be generic in nature, the goal of which is to monitor general aspects of the patient's health, such as, for example, "how are you feeling today?" or "have you taken your medication yet this morning?" As will be explained in further detail below, depending on the response received, more specific queries may be provided subsequently. For example, if a patient's response to a first patient-specific query asking "have you taken your osteoporosis medication yet today?" is "yes," but correlated passive data indicates the patient has not picked up a new prescription from the pharmacist (using passive data from the PBM database and/or geolocation data of the patient), a second patient-specific query may be provided to the patient, such as, for example, "Do you have excess medication left over from a previous prescription?"

In some embodiments, first patient-specific queries may be in the form of more standardized survey batteries in pain and functionality, such as, for example: Pain Quality Assessment Scale (PQAS), face/symbol scales (e.g., happy face equals low pain, frowning face equals moderate pain, sad face equal intense pain, etc.), 1-10 numeric scales, Leeds Assessment of Neuropathic Symptoms and Signs (LANSS), use of interactive anatomic charts to map sites of pain and/or occurrence of symptoms, PROMIS Pain Behavior Scale, PROMIS Physical Function SCALE, Global Impressions of Satisfaction and Change in Pain Management, etc. Additionally, first and/or second patient specific queries may be associated with different categories of information or topics. For example, in addition to, or in place of, survey batteries, information processor 110 may generate the following: queries about exercise—e.g., type, timing, intensity, perceived exertion; queries about rehabilitation—e.g., type, intensity, perceived exertion; queries about diet—e.g., content, quantity of nutrients, (grams of fat, carbohydrate, etc.), time of meals, body weight, anthropomorphic measurements (waist size, etc.); queries about lifestyle—e.g., sleep timing, sleep duration, sleep quality, tobacco intake, alcohol intake, caffeine intake, social interactions, family interactions, caregiver interactions. In some embodiments, first patient-specific queries may be generated from any of the standard batteries, whereas a second and/or third etc. patient-specific query may be generated from a specific category as described above.

In some embodiments, first patient-specific queries are selected and provided from a list of queries in a database that can be associated with the patient and the patient's health profile, and/or that can be predefined by the HP. Additionally, second patient-specific "follow-up" queries can also be selected and provided in a similar manner, and/or can be dynamically generated based on algorithms interpreting the patient's response to the first (or any prior) patient-specific query. In yet other embodiments, associated queries can be predefined, and, depending on the response received to a first query, information processor 110 can automatically propagate a second associated query. Furthermore, in some embodiments, additional (third, fourth, fifth, etc.) patient-specific queries can be provided responsive to the patient's response. Additional queries can be newly generated/propagated queries (queries not yet sent to the patient in relation to a given survey) or a repeat of a previously provided query can be re-sent. This can be determined by information processor 110 to be necessary, for example, if the patient is unresponsive to a first patient-specific query, or if a received response is incoherent. Successive queries can be narrower in scope, broader in scope, and/or may be substantively different from the first patient-specific query.

In some embodiments, sets of queries can be provided in the form of a query tree or hierarchy, wherein, depending on the response to a query on a 'first level' of the query hierarchy, one or more of a plurality of 'second' level questions may be provided, etc. Alternatively or additionally, queries and/or responses can be accorded weights, points, or scores (collectively "scores") for use by an NLP algorithm or any other appropriate algorithm within information processor 110. Depending on a calculated score based such queries/responses, information processor 110 can determine whether particular follow-up queries should be provided, and/or whether other actions must be taken. This may be critical, for example, where no one response warrants serious concern or alarm, but where a combination of responses may together paint a more serious picture. Of course, the opposite is also true: individual responses or other data collected may not alone show improvement in health or more effective care, but a combination of responses or other data may.

Once a patient-specific query has been provided to patient 210, AD module 145 receives and parses any AD received from patient 210 at step 412, including metadata such as the time and date that the response was provided. Concurrently or asynchronously, PD module 150 receives and parses any PD received from the patient 210 at step 413, via sensors in mobile device 114 and/or from specialized sensor 115, including metadata such as the time and date of the receipt of the data, the geolocation of the user, ambient information if available (including temperature, background noise level, humidity, light level, and so on). At step 415, any data (both AD and PD) is scanned by monitoring module 165 for irregularities. In some embodiments, irregularities may include any changes in measured metrics from whatever is determined by the code executing in the module as being the baseline, which may be predefined by HP 230, by the patient 210, or by a third party, such as an ACO of which HP 230 is a part, or a third party payor (e.g. health insurance provider). Measured metrics may include, for example, the following: rapidity of texting/typing on a patient device; frequency of texting/typing/emailing on a patient device; frequency of phone calls/social media interaction; rapidity of answering surveys/prompts; weight gain/loss; number of steps taken; distance traveled, e.g., on foot or by bicycle, etc. (unrelated to transportation by car, bus, taxi, etc.); sleep dynamics; and appetite and food/calorie intake.

Furthermore, irregularities may be statistical or situational. Statistical irregularities may include, for example, data that is determined to be outside of a data range or data set that would be typically expected for patient 210 and/or similarly situated patients (similar illness, treatment, demographic, etc.), or as may be determined by the HP (e.g., two standard deviations from the norm). For active data, this might, for example, include a detection by the NLP algorithm that a patient's speech is slurred in a vocalized response, or the patient responding that he or she did not take medication on a given day. For passive data, this may include a detection of a spike in a patient's temperature, or drop in heart rate. Examples of situational irregularities may a detection that a patient who is typically known by the system to be active during daytime hours has not moved for a predefined period of time during the day.

Accurate detection of statistical and situational irregularities can be "learned" by the information processor 110 using Artificial Intelligence (AI) algorithms (such as the NLP algorithm) to process data and detect when data is comparatively abnormal. Regardless, if an irregularity is detected at step 115, in some embodiments the patient-query module 160 may generate a "follow-up" second patient-specific query and provide the follow-up query to patient 210 at step 411. In some embodiments, in addition to, or instead of patient-query module 160 generating a follow-up query, at step 430 HP 230 may be notified of the irregularity by alert module 170. At step 431, HP 230 may then determine, via scheduling module 175, whether to generate an HP-generated query at step 432, or to schedule an appointment without further queries being generated.

If no irregularities are detected in the received AD and received PD, or if irregularities detected do not fall with the predefined data range or set, then at step 420 AD/PD correlation module 155 correlates the received AD with the received PD. In accordance with some embodiments of the invention, AD/PD correlation may be accomplished by comparing data actively provided by patient 210 with passive data collected through sensors associated with patient 210, and analyzing the comparison relative to a predefined correlation threshold, to assess if the data accurately correlates within the predefined correlation threshold. In accordance with some embodiments, a correlation threshold may be understood as a level of tolerance when correlating multiple data points or sets, e.g. comparing, contrasting, or otherwise analyzing characteristics of different data, and in some instances the correlation can encompass a change that is identified relative to a baseline value or range for the patient or for a demographic that includes the patient.

In some embodiments, AD/PD correlation may include comparing and/or otherwise validating the data to be correlated by the AD/PD correlation module 155, such as by using time stamps (PD) of geolocation tags (PD) indicating where a patient was located at a specific time to validate a patient's express recollection of where the patient was at that time (AD). In some implementations, a predefined correlation threshold may include, for example, a window of time (e.g., within 'x' number of minutes between what a patient reports and what is detected by the sensor), and the AD/PD correlation module 155 can determine if the provided time and the detected time are within the predefined window of time. If, for example, the patient indicates that she awoke from bed at 9:30 AM (AD=9:30 AM), and accelerometer data indicates significant movement by the patient at 9:33 AM (PD=9:33 AM), and the predefined correlation threshold is 5 minutes, then AD/PD correlation module 155 can perform the following calculation:

$$9:30\ AM-9:33\ AM=(+/-)\ 3\ minutes \leq 5\ minutes \rightarrow data\ successfully\ correlates\ with\ the\ predefined\ correlation\ threshold.$$

In some embodiments, one or more correlation thresholds can be employed. For example, a query can ask a patient whether the patient has walked a mile (distance=X) this morning. PD collected and time-stamped by a pedometer provides the AD/PD correlation module 155 with a number of recorded steps (steps=Y) and date/time information relating to those steps (time=Z1, Z2, etc.). If the average person takes around 2,000 steps in a mile (X=2000Y), and the patient claims to have walked a mile this morning, then a first correlation threshold (CT1) in this example can be a tolerance of ~50 steps (e.g., 1950Y≤CT1≤2000Y). Alternatively, the pedometer can provide a mileage number as the output. A second correlation threshold (CT2) in this example can be a time range during which each time stamp Z1, Z2, etc., should fall (e.g., CT2=<6:00:00 AM-11:59:59 AM>). In this example embodiment, AD/PD correlation module 155 can determine both whether patient 210 took the requisite number of steps (within CT1), and whether those steps were taken during or close enough to the morning hours of the day (within CT2), in order to validate the patient's claim to have (a) walked a mile, and (b) completed the task of walking a mile during the morning.

In some embodiments, AD/PD correlation may be a comparison of two or more data points (e.g., a measurement of how close or far apart multiple data points are, as in the example above), or may be a determination of whether a data point falls within a predefined data set (such as, for example, whether a patient was actually within a predetermined location when the patient said he or she was). Therefore, examples of a predefined correlation threshold may include a single value, a set of values, or a value range as may be necessary to determine whether AD and PD correlate. This may be used, for example, to indicate a predefined allowance for error in reporting of active data and/or passive data, and to monitor accuracy of AD and/or PD provided by the patient 210 and sensors associated with the patient, etc. Of course, it will be understood by those of ordinary skill in the art that different mathematical operations can be required to be performed depending on the nature of the AD and PD collected, and the type of monitoring that is required for different types of data, and that the example equation provided is therefore not intended to be limiting.

For example, AD/PD correlation module 155 may correlate GPS location data (PD), which may be monitored using geolocation module 180 and received from mobile device 114, with an affirmative response to a query as to whether patient 210 went to an exercise class (AD). A predefined correlation threshold in this instance may be defined by how close the patient's geolocation data should indicate that the patient actually came to the known geographic coordinates of a local exercise center in order for the patient to be "confirmed" as attending the class. In some embodiments, AD/PD correlation module 155 may be preconfigured to extract predefined classes or types of AD and PD for correlating. Additionally or alternatively, AD/PD correlation module 155 may intelligently classify and correlate received AD and PD based on other correlating and/or corresponding information. For example, mobile device 114 may have been turned off by patient 210 while traveling to and attending a physical therapy session, but a receipt for a water bottle purchased at a store near the physical therapist may provide corroborating PD in place of GPS tracking data.

In some embodiments, AD/PD correlation module 155 can be provided with a correlation threshold by the HP 230, by the patient, by a third-party (ACO, IDN, etc.), and/or may be dynamically generated based on previously collected patient and/or patient population data using AI algorithms as described above. In some embodiments, in determining an appropriate correlation threshold for chronic illness, baselines for both AD and PD are first determined, and then a baseline representing an acceptable tolerance (the correlation threshold) in differences between received AD and received PD is defined. For example, baselines in the following types of data may be assessed for received AD, received PD, and the appropriate correlation threshold: mobility related baselines, e.g., number of steps climbed, number of blocks walked, minutes of exercise per day, etc.; and symptom related baselines, e.g., amount of sleep, absolute pain scores, amount of time that a patient would characterize as the "worst," best recollection of what treatments/actions help relieve symptoms; ability to lie in bed (upright/flat), stress levels, etc.

At step 421, AD/PD correlation module 155 determines whether the correlation data generated by AD/PD correlation module 155 meets the correlation threshold, and if not, then the method continues with additional queries being generated at step 411 and/or HP 230 being notified at step 430. If AD/PD correlation module 155 determines that the data generated by the correlation meets the predetermined correlation threshold, then at step 422 monitoring module 160 continues monitoring, all data is stored at step 440, and the method repeats at step 410. It should be noted that AD, PD and/or correlation data, can be stored at any stage of the method.

As longitudinal data is collected and saved, certain data may be anonymized at step 450 for purposes of further analyzation, while protecting patients' identities. For example, at step 450, data anonymizer module 195 may anonymize correlation data related to a plurality of patients, and at step 451, patient correlation module 185 may correlate the data of the plurality of patients to create meaningful statistical analysis that can then be provided to the patient in the form of feedback at step 460, and/or to the HP 230, to an ACO to which HP 230 belongs, and/or a third-party payor, etc., to aid in the healthcare management of the plurality of patients. In addition, data relating to the treatments (prescriptions, diet, exercise, etc.) of a plurality of patients provided by the HP 230, and/or data identifying the HP 230, can be anonymized, and a plurality of HP-generated data can be correlated at step 452, which can likewise be provided to patients, HPs, ACOS, IDNs, hospital networks, and/or other third parties (insurers, government agencies, etc.) at step 460. As with the AD/PD correlation and correlation threshold described in detail above, correlation thresholds can similarly be determined for the correlation of data collected from a plurality of patients and/or healthcare providers at steps 451 and 451 respectively.

In some embodiments, code executing in feedback module 198 can be transmitted across network 112 to patient device 114, patient computer 113, HP 230, or any combination thereof, to provide text, email, voice alerts, data for use within an application, etc., at the desired recipient of the feedback. Furthermore, feedback module 198 can provide feedback in the form of computer code to other systems, computers, servers and/or databases, or any other computing device, over network 112, which cause the recipient computing device to perform additional functions as required. For example, feedback module 198 can, in conjunction with scheduling module 165, provide feedback to a scheduling module in a processor of a third party computing device, such as a mobile device of an attending physician, causing an appointment to be entered in a calendar application operating on the physician's device.

In some embodiments, whether data is anonymized before being correlated and/or provided to a particular party in the form of feedback may depend a level of access rights assigned to the party. For example, patient 210 may allow a third party insurance company to receive notifications/feedback relating to the patient in exchange for lower premiums. By providing AD/PD correlation data to the insurer, the patient is better able to show that he or she is actively managing their healthcare. However, an unrelated HP may only have access rights to anaymized data for purposes of providing better care to patients and better allocating resources, without violating HIPAA compliance and/or other regulations.

In some embodiments, referring back to step 431, should HP 230 determine that an appointment should be coordinated for patient 210, at step 433 a critical-level indicator may be dynamically generated by scheduling module 175, in response to the severity of the irregularity, correlation failure, and/or other patient related data, and assigned to patient 210. A critical-level indicator may indicate, for example, how critical it is for a patient to be seen by HP 230 in a timely manner (e.g., as soon as possible), or how critical it is for a patient to be seen at a particular point in time (e.g., later-in-time, but critical that the patient be seen at the scheduled time). Using critical level indicators of a plurality of patients being monitored on the HP's dashboard, the scheduling module 175 can determine which patients are a priority by ranking the plurality of patients. At steps 434 through 439, scheduling module 175 coordinates patient/HP appointments for the plurality of monitored patients based on the priority rankings, and informs other patients if and when their appointments have been re-scheduled.

Figure 5:
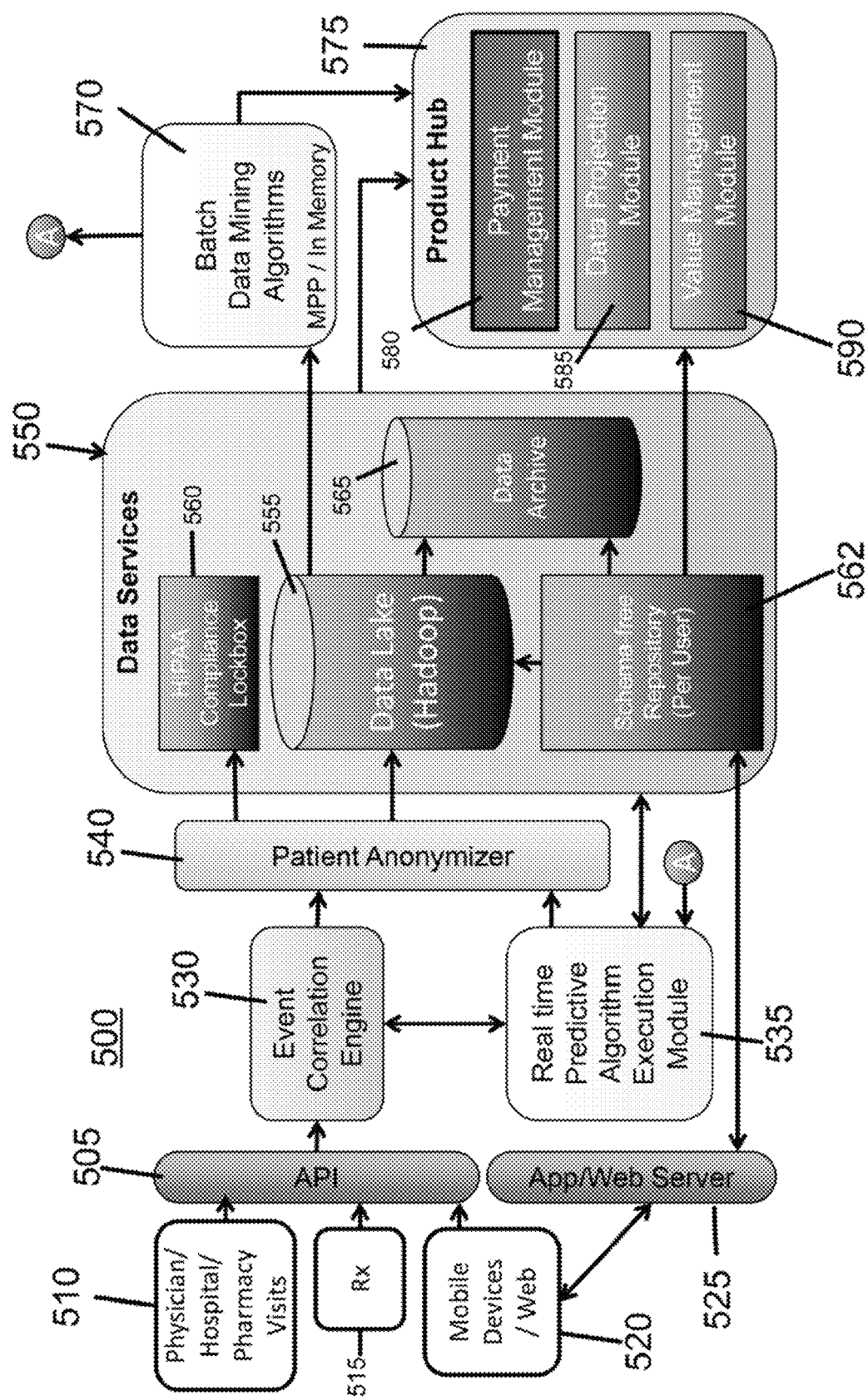
FIG. 5 is a schematic diagram illustrating another perspective of a system for supporting health management services according to at least one embodiment according to the invention.

Turning now to FIG. 5, the code executing in the processor 120, including one or more of the modules from the instruction storage device 140, is described in relation to major functional blocks that can define a system 500 in accordance with an embodiment of the invention. The system 500 is accessed through a data collection layer that comprises one or more APIs by a variety of users (stakeholders) including physicians, hospitals, pharmacies, and patients. Principal components of the system can be included in the information processor 110 described in connection with FIG. 3. As illustrated, access to the system 500 can be through one or more front-end portals that are configured for each user type, such as by application program interface (API) 505. The API can support custom portals that include authentication fields, data upload provisions, and so on. The portal for a physician 510 accessing the system can be configured differently than one intended for access by a pharmacist 515 or one intended for a patient 520, or even for a payer for that matter. The API is published so that third parties can develop to suit their particular requirements.

The portal is the interface to the system, and as such can be tailored to meet the needs or preferences of each user type, and can be constructed in accordance with schema-free database configuration for each of the stakeholders to provide fields of data that need not match a prescribed schema, as understood by those having ordinary skill in the art. Moreover, the portal can comprise an interface provided through a webpage or a mobile-adapted page, as two non-limiting examples. Additional APIs can be provided, such as API 525, which can comprise app servers which are configured to receive data and to feed data to the user through a web browser or a dedicated program such as a mobile application. Data including alerts, notifications, reports and other summaries can be provided to users on the devices 113, 114, etc. through an API that is separate from the API that is used to receive the active and passive data described above. Optionally, the API(s) can support connectivity to specific solutions that have relevance to subgroups of a given user-type. For instance, for patient-users, apps can be provided which focus around a particular problem such as acute pain, diabetes, as two non-limiting examples. Also by way of example and not limitation, for physician-users, apps can be provided which focus around particular disciplines such as nephrology or oncology. Likewise, the API for a subgroup such as physicians can be configured by code to mirror alerts that have been sent to a given physician's patient (e.g., as a result of operation of the monitoring module 165 and the alert module 170, described above), but not mirror that alert to another user-type, such as the payer.

The APIs 505, 525 are configured to receive information from the user and provide it to one or more correlation engines, shown schematically as event correlation engine 530. The event correlation engine can encompass one or more of the correlation engines described previously, including the AP/PD correlation module 155, the patient correlation module 185, and the HP correlation module 190. The event correlation engine 530 is provided with data from a plurality of user-types and that information is acted upon by a real time predictive algorithm execution module 535. In particular, the event correlation engine 530 is communicatively coupled to the real time predictive algorithm execution module 535, which comprises code that configures a processor to produce actionable information from the data stream received at the event correlation engine from users that are connected over a network connection via the API. In the meantime, both the engine 530 and the module 535 provide data to one or more data services 550. However, some of the data is passed through a patient anonymizer 540 which is a module that comprises code that configures a processor to transform patient-specific data that has been received through one or more APIs, after processing by the engine 530 and module 535, into a form that has the patient-identifiable elements removed (e.g., name, home address, possibly the raw values such as precise age, precise weight, and so on). In lieu of the patent-identifiable elements, a sequential number can be assigned to enable different data nuggets to be matched to the same anonymized person. The engine 530, the predictive algorithm execution module 535, and the patient anonymizer module 540 can all operate as substantially real-time processes, sending data to the data services 550 which are discussed next.

The data services 550 comprise a plurality of data stores and can be implemented in a Hadoop cluster or in any other storage configuration as may be appropriate to a given implementation. A data lake 555 receives the anonymized data from the anonymizer 540, and this data is stored and made available to multiple resources having authorization to access it. Meanwhile, a HIPAA compliant, tightly controlled data repository, which includes the information in the data fields received over the network by the event correlation engine 530, is maintained in a HIPAA compliant lockbox (data storage) 560. The data received over the network can be stored for each user in a schema-free repository 562 in support of database operations that are configured to operate without a prescribed data schema and which are managed using the sequential number that has been assigned, as described above. Likewise, a data archive can maintain the data for retrieval in a conventional manner.

The data services 550 can be accessed by various modules such as the product hub 575 (discussed below) and the predictive algorithm execution module 535. The arrows in FIG. 5 are illustrative of possible data flows, but whether there is a single-direction arrow or an arrow leading to the data services 550 in general, or to a particular repository is not limiting of a different embodiment within the scope of the a particular embodiment of the invention which may differ from the embodiment illustrated in this figure. Other arrangements can be constructed to provide the functionality discussed herein.

The system 500 can include other processing systems for supporting health management services. For instance, one or more batch data mining algorithms 570 can be provided which, like the real-time predictive algorithm execution module 535, can implement machine learning algorithms that utilize statistics and probability to arrive at predictions that drive actions to be taken, such as by the product hub 575. Numerous such algorithms are known, and can be employed in a massively parallel processing configuration, including cloud-based arrangements, to execute against the anonymized data in the data lake 555 and thereby drive the product hub 575 to an output with information of value to a given stakeholder such as a physician or payer. For instance, the batch data mining algorithm 570 can be used for hypothesis formation, verification and creation of other algorithms. Data visualization engines (not shown) can be incorporated in a particular embodiment to operate on the mined data. The particular solution to be employed optionally can take into consideration the CAP theorem with the solution configured to trade consistency for availability and partitioning tolerance. It is to be understood that alerts, reports, and various predictions that a patient may require treatment now, or is not following a proper regimen, etc., can be responsive to predictive algorithms, as noted above, and that the algorithms can take into consideration the real-time part from the real-time predictive algorithm execution module 535, and also the batch part from the batch data mining algorithms 570 which looks to historical data from the data lake 555 or from other data services 550 available to the system 500, and more particularly to the information processor 110 that is implementing this functionality.

The product hub 575 provides a variety of outputs of the system 500, one or more of which can be triggered by interaction with a front-end portal or app through the APIs 505, 525, or by operation of the batch data mining algorithms 570, or by interaction with a separate portal that provides information to a given user. The product hub includes one or more modules that provide the functionality described next through the execution of code that configures a processor to operate as described next. The payment management module 580 can be used by payers and other users to manage the information concerning the correlations, alerts and other information collected and processed from the active and passive user data, and from actions by physicians and prescribers that correlate to such patient data. Among other things, such data can validate the value of the correlated information. The data projection module 585 can extrapolate data that was collected from one group, say, from a group of users with acute pain all of whom live in Massachusetts, to a larger group, say, all of America. The value management module 590 can produce data summaries that have value to third parties such as manufacturers, and so on. Moreover, that module can produce data in support of a value proposition in connection with any particular therapy.

Figure 6:
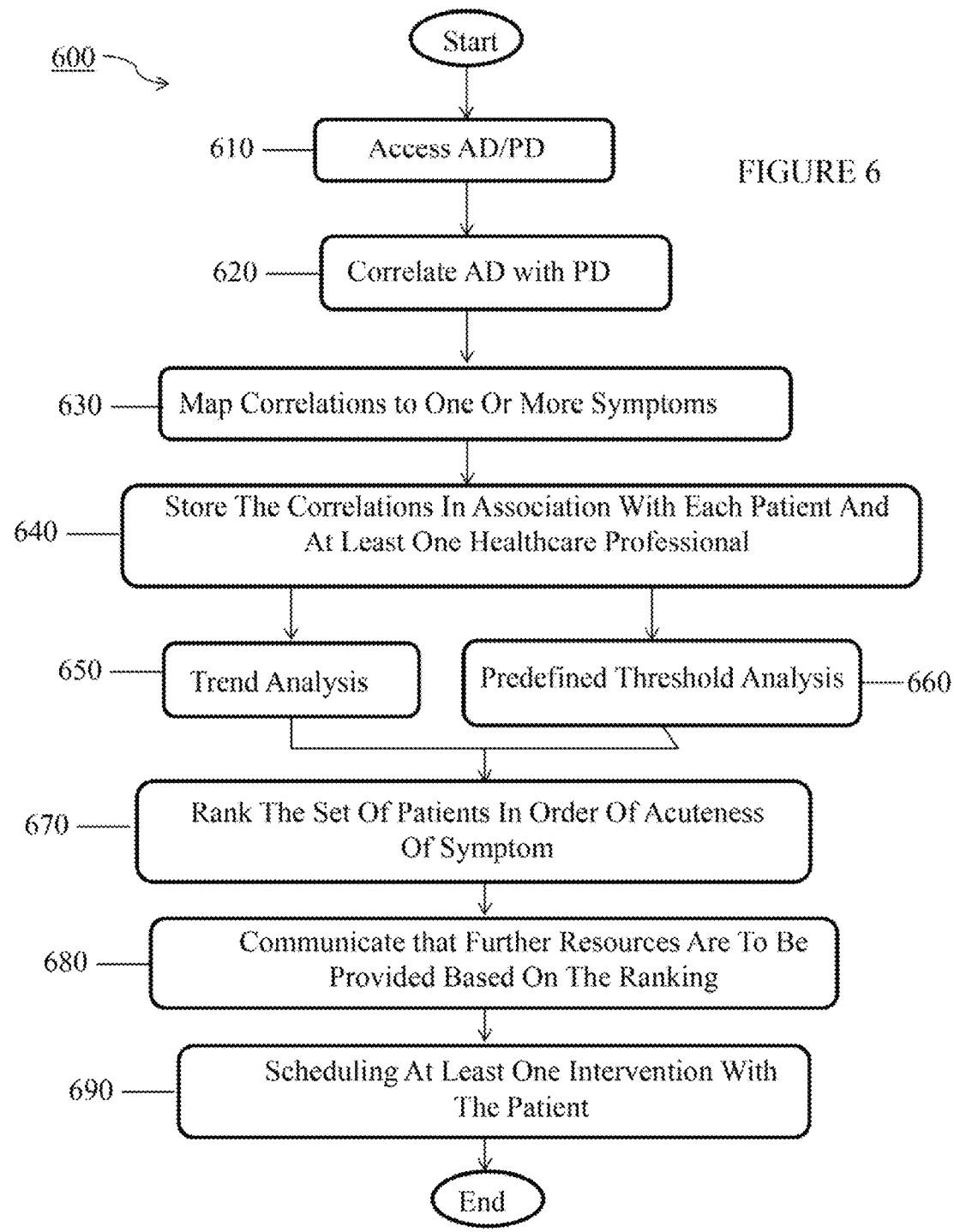
FIG. 6 is a flow diagram illustrating a process in support of analyzing health management services provided by a plurality of healthcare professionals according to at least one embodiment of the invention.

Turning now to FIG. 6, a further aspect of the invention is concerned with analysis of the active and passive data of the type discussed hereinabove. As previously described, the active and passive data can be accessed by the information processor 110, as indicated at step 610 and correlated with one another, as indicated at step 620. Access to the data can be by accessing a database or table in which the data is stored, in a conventional manner. The database can be within and among the data services 550 discussed above. The correlation is performed by the AP/PD correlation module 155 at the processor 120. As indicated at step 630, the correlations can be mapped to one or more symptoms, by a portion of the AP/PD correlation module 155, and/or by other code executing in the processor. The mapping can be accomplished by reference to a rule base that contains rules that relate each symptom to particular data/data sets. The rules in the rule base match the particular type of active data and passive data being correlated with one another. As a function of the individual definitions of each rule, particular data can be mapped exclusively to one symptom if the rule base resolves to a single symptom matching the data, whereas other data can be mapped to multiple symptoms if the rule base resolves to several symptoms. Each type of data being accessed and utilized by the correlation module has characteristics that enable its processing by such rules. In some embodiments the correlations are stored in a database such as within the resources of the data services 550, in an anonymized or HIPAA compliant manner so as to maintain an association with the patient from whom the accessed data was collected. The correlations can also be stored in association with at least one healthcare professional, namely, a healthcare professional who is already associated with the care of the person from whom the accessed data was collected, or who later becomes associated with the care of that person.

In accordance with this aspect of the invention, the processor 120 is further configured by code such as executing in the AP/PD correlation module 155 to analyze the correlations in support of providing or managing health-related services. The correlation module 155 can configure the processor using code executing therein to identify trends in the active and passive data pairs, as indicated at step 650. For instance, if the accessed data shows a patient actively reporting a progressively worsening condition while the passive data is providing consistent information (e.g., lack of movement, certain blood pressure readings, and so on), there may be a correlation between the AD and the PD which keeps it within a prescribed threshold correlation, yet the trend of the data that is being analyzed by the module 155 indicates that an intervention by a healthcare professional is warranted. Such trend analysis applies to each of the embodiments and arrangements described herein, and can be made in conjunction with or as an alternative to having the correlation module 155 executing code in the processor which identifies whether there is a mismatch between the individual data elements and determines whether the correlation between the active data and the passive data falls outside of a predefined correlation threshold (step 660).

Operation of the correlation module 155, according to this mode of the invention, identifies a set of patients among all those being reviewed that have trend changes related to a particular symptom, who have correlations that are swinging outside of a predefined correlation threshold for the particular symptom, or both.

Each patient can be known to the data services 550 as having an individual degree of acuteness of the particular symptom that has been reported to their healthcare professional (HIP), and possibly a variety of symptoms. (As well, the patients might exhibit objective signs which can be recorded and maintained in the data services 550 too.) The set of patients that are identified by operation of the AP/PD correlation module 155 can be ranked in order of most acute to least acute for a given symptom by processing the data in the data services that bear on this parameter, as indicated at step 670, when such information is available, and default values based on historical use of healthcare services can inform the ranking module. For instance, regardless of whether there is data to ascertain the acuity of the patient's symptom, the AP/PD correlation module 155 can include code that configures the processor to review, as non-limiting examples, the frequency of visits, the date of a last visit, the total number of visits, the resources that were used in connection with those visits (e.g., lab tests), and so on, in connection with the arriving at a position for the patient in the ranking. The relevant data can be stored, by way of example and not limitation, in a medical record and can include the active data received from the patient, passive data received from the patient, information input by the HP, and other data. To the extent that some of the data is in textual form, an NLP algorithm can provide probabilistic weightings that can be used in the ranking of one patient in the set to others.

At least a portion of the patients in the set, such as those having the most acute symptom(s), can be targeted for having further resources provided to those patients by a healthcare professional, such as that patient's doctor, based on the ranking determined above. A communication can be sent over a distributed computer network, such as network 112, to the HP or to the healthcare network affiliated with the HP that further resources are to be provided to at least that portion of the ranked patients, as indicated at step 680. The further resources can take a variety of forms, including a direct communication from the HP to the patient to investigate the reason that the patient was identified as a result of operating the AD/PD correlation module 155, sending an ambulance to the patient (and the PD may identify a current location of the patient), scheduling one or more interventions by the healthcare professional with the patient, triggering a phone call or other alert on the part of the clinical team supporting the HP, or arranging an urgent visit or a visit by telepresence, as indicated at step 690.

In this manner, healthcare services can be provided to patients in a just-in-time manner and the care being provided can be managed and statistically tracked. Moreover, through code executing at the information processor 110, the acuity of patients can be taken into consideration and used to normalize (e.g., weight) the data about the healthcare services that have been delivered to patients having different resource requirements. As such, balanced analytics can be output by the information processor 110 that enables more precise comparisons of the effectiveness of one healthcare professional to another, and/or of one healthcare network to another, and comparisons of the protocols being applied by different HPs and healthcare networks and the timing of healthcare service delivery and other parameters in support of managed healthcare services. At this juncture, it should be noted that although much of the foregoing description has been directed to systems and methods for providing support for healthcare management services, the systems and methods disclosed herein can be similarly deployed and/or implemented in scenarios, situations, and settings far beyond the referenced scenarios. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a computer implemented method, computer system, and computer program product for providing augmented content. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The functions describe herein can be implemented by hardware and or hardware executing code (also known as programs, software, or software applications) which include machine instructions for a programmable processor, and can be implemented in a high-level procedural and/or object-oriented programming language, and/or in assembly/machine language. As used herein, the terms machine-readable storage medium and computer-readable storage medium refer to any computer program product, apparatus and/or device (e.g., magnetic discs, optical disks, memory, Programmable Logic Devices (PLDs)) used to provide machine instructions and/or data to a programmable processor, including a machine-readable storage medium that receives machine instructions as a machine-readable signal. The term machine-readable signal refers to any signal used to provide machine instructions and/or data to a programmable processor. A machine-readable storage medium does not include a machine-readable signal.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any implementation or of what may be claimed, but rather as descriptions of features that may be specific to particular embodiments of particular implementations. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method in support of health management services for a patient, the method performed by a hardware device having a processor and memory having processor executable code that, when executed by the processor, causes the hardware device to:
   (a) monitor the patient by:
      receiving passive data of a first type detected by at least one patient sensor from the patient, the passive data being associated with metadata concerning at least a time of the passive data detection;
      receiving active data that represents an affirmative response to a first patient-specific query that has been provided to a user interface of a device associated with the patient, the active data being associated with metadata concerning at least a time of active data receipt; and
      storing the received passive data, the received active data, and the metadata associated with the received passive data and the received active data;
   (b) validate the received passive data and the received active data by:
      comparing a portion of the received passive data to a portion of the received active data on the basis of the time in the metadata associated with the passive data and the active data, respectively; and analyzing the data that was compared on the basis of the time in the metadata relative to a correlation threshold in order to assess whether the compared data correlate with the correlation threshold, wherein the correlation threshold comprises a threshold value, set of values or value range of a change relative to a baseline value or range;

(c) repeat the monitoring and validating steps if the compared data correlate with the correlation threshold, else, if the compared data does not correlate with the correlation threshold:

receive further passive data of a second type that is different than the first type and which is detected by a different sensor;

determine compliance and/or patient veracity in connection with health management based on the analysis of the compared data and an analysis of the received further passive data; and in the event of the determination being either non-compliance or lack of patient veracity, generate a non-correlation notification and provide the non-correlation notification to a respective device associated with at least one of the patient, a healthcare professional, and a third-party.

2. The method of claim 1, wherein the hardware device is further configured to dynamically generate the correlation threshold based on the received passive data, the received active data, or both.

3. The method of claim 1, wherein the received further passive data includes metadata concerning a time of the further passive data detection, and wherein the code, when executed the processor, causes the hardware to repeat the monitoring and validating in the event that the compared data does not correlate with the correlation threshold, further causes the hardware to:

generate a second patient-specific query which corresponds with at least the received further passive data;

deliver the second patient-specific query to the device associated with the patient to be provided to the patient in the user interface; and receive further active data and metadata concerning the time of the active data receipt, the further active data representing an affirmative response to the second patient-specific query in the user interface, wherein the determination of compliance and/or patient veracity in connection with health management is based on the analysis of the compared data, the analysis of the received further passive data, and an analysis of the further active data.

4. The method of claim 3, wherein the second patient-specific query generation comprises:

regenerating the first patient-specific query and the processor executing code to generate the second patient-specific query.

5. The method of claim 1, wherein the generation of the non-correlation notification includes providing information reflecting the non-compliance or lack of patient veracity.

6. The method of claim 1, wherein the hardware is further configured to:

generate a correlation notification if the compared data correlates with or within the correlation threshold; and provide the correlative notification to a respective device associated with at least one of the patient, a healthcare professional, and a third-party.

7. The method of claim 6, wherein the hardware is further configured to:

receive diagnosis/treatment data responsive to providing the notification to the healthcare professional; wherein the diagnosis/treatment data represents at least one of a diagnosis, a treatment plan, a healthcare professional-query, and an observation relating to the patient;

store in the memory the diagnosis/treatment data and at least one of the received active data, the received passive data, compared data, and correlation data generated by the analyzing the compared data relative to the correlation threshold of the received active data with the received passive data;

anonymize the diagnosis/treatment data and the at least one of the received active data, the received passive data, compared data, and correlation data into a form that has patient-identifiable elements removed;

correlate the anonymized diagnosis/treatment data and the anonymized at least one of the received active data, the received passive data, and the first correlation data;

correlate the anonymized diagnosis/treatment data with other anonymized diagnosis/treatment data of at least one other healthcare professional;

generate anonymized diagnosis/treatment data reflective of data generated by the correlation of the anonymized diagnosis/treatment data of the healthcare professional with the other anonymized diagnosis/treatment data of the at least one other healthcare professional; and present the anonymized diagnosis/treatment data to at least one of the patient, the healthcare professional, the at least one other healthcare professional, an accountable care organization to which the healthcare professional belongs, and a third-party payor.

8. The method of claim 6, wherein the hardware is further configured to:

determine based on predefined scheduling criteria whether to schedule a patient appointment with the healthcare professional;

upon a determination not to schedule a patient appointment with the healthcare professional:

generate a healthcare professional-query; and deliver the healthcare professional-query to a device associated with the healthcare professional; and upon a determination to schedule a patient appointment with the healthcare professional:

generate a critical-level indicator associated with the patient;

receive patient-calendar information associated with the patient;

coordinate the patient-calendar information with received healthcare-professional scheduling information responsive to the critical-level indicator;

wherein a first patient is prioritized to be seen by a healthcare professional sooner in time than a second patient, when the first patient has a higher associated critical-level indicator than the second patient; and determine an agreed-upon appointment.

9. The method of claim 1, wherein the code, when executed the processor, causes the hardware to monitor the received passive data further causes the hardware to:

identify any predefined irregularities in the received active data and the received passive data; and generate a second patient-specific query which corresponds with at least the irregularities in the received passive data, wherein the monitoring of the received active data comprises receiving the second patient-specific query active data which corresponds to an affirmative response to the second patient-specific query.

10. The method of claim 9, wherein, upon identifying at least one least one irregularity and in the event of the determination being either non-compliance or lack of patient veracity the notification generation step includes, further code configures the hardware to generate an irregularity notification reflecting the irregularity or failure.

11. The method of claim 1, wherein the validation step further comprises:
   anonymizing at least the compared data into a form that has patient-identifiable elements removed;
   wherein the analyzing step includes correlating the anonymized data relative to an anonymous correlation threshold to assess whether the anonymized data correlates with or within the anonymous threshold correlation, wherein the anonymous threshold correlation value comprises a threshold value, set of values, or value range of change relative to a base line value or range relative to at least one other patient, and
   wherein the hardware is further configured to provide at least the anonymized data and whether the anonymized data correlates with the anonymous threshold correlation to a respective device associated with at least one of the patient, a healthcare professional, and a third-party.

12. The method of claim 1, wherein the hardware device is further configured to, in regard to the monitor of the patient:
   generate the first patient-specific query by selecting and providing the first patient-specific query and delivering the first patient-specific query to the device associated with the patient.

13. The method of claim 1, wherein the metadata associated with at least one of the passive data and the active data further concerns GPS location data, and further wherein the correlation threshold is further defined by a distance range, and still further wherein the compared data does not correlate with the correlated threshold when distance represented by the GPS location data is outside of the distance range.

14. The method of claim 1, wherein one of the received passive data and the received further passive data include GPS location data.

* * * * *